United States Patent [19]

Bergelson et al.

[11] Patent Number: 4,493,327
[45] Date of Patent: Jan. 15, 1985

[54] AUTOMATIC EVOKED POTENTIAL DETECTION

[75] Inventors: Michael Bergelson, Port Chester; Jacob Fridman, Kew Gardens; Erwin R. John, Mamaroneck, all of N.Y.

[73] Assignee: Neurometrics, Inc., New York, N.Y.

[21] Appl. No.: 400,150

[22] Filed: Jul. 20, 1982

[51] Int. Cl.³ .............................................. A61B 5/04
[52] U.S. Cl. .................................... 128/731; 364/417
[58] Field of Search ................. 128/731, 732; 364/417

[56] References Cited

U.S. PATENT DOCUMENTS

| | | | |
|---|---|---|---|
| 3,901,215 | 8/1975 | John | 128/731 |
| 4,214,591 | 7/1980 | Sato et al. | 128/731 |
| 4,275,744 | 6/1981 | Thornton et al. | 128/731 |
| 4,408,616 | 10/1983 | Duffy et al. | 128/731 |

OTHER PUBLICATIONS

Boston, J. R., Younger, C. A., "Spectral Estimates of Auditory Brainstem Responses", *Third Annual Symp. on Comp. Appl. in Med.*, IEEE Wash. D.C., Oct. 14–17, 1979, pp. 691'4 696.

Primary Examiner—Kyle L. Howell
Assistant Examiner—Christine A. Fukushima
Attorney, Agent, or Firm—Cooper, Dunham, Clark, Griffin & Moran

[57] ABSTRACT

Disclosed are a method and a system for determining if a patient's brain electrical activity reflects a significant evoked response to a sensory stimulus. A test measure of the difference between two sets of averaged waveforms, one in the absence and another in the presence of the stimulus, is derived on the basis of (i) mean values of spectral measures of the two sets and (ii) the variance of these spectral measures. This test measure is matched against acceptance and rejection levels which are defined on the basis of both (i) the number of averaged waveforms in each set and (ii) the desired degree of probability of avoiding false positive or false negative results.

20 Claims, 13 Drawing Figures

Fig. 5A.

AUTOMATIC EVOKED POTENTIAL DETECTION

BACKGROUND AND SUMMARY OF THE INVENTION

The invention relates to diagnostic testing which involves detection of brain electric response to presentation of stimuli, e.g., auditory or electric.

It has long been known that time-varying spontaneous electrical potentials (SP) exist between different areas of a patient's scalp, and that a record thereof, called an electroencephalogram, or EEG for short, can be studied in an effort to relate them to the patient's brain activity. It is also known that when the patient is subjected to certain stimuli, a time-varying evoked potential (EP) tends to be superimosed on the normally present EEG voltages. For example, an auditory stimulus in the form of a click heard by a patient, tends to superimpose an oscillatory component on the SP. Similarly, an electric shock to the skin tends to superimpose an oscillatory component. The EP oscillation tends to be time-locked to the stimulus. Different stimuli tend to produce evoked potential signals with different anatomical distributions on the scalp and with different waveshapes.

The detection of evoked potentials and of the physiologically significant information therein is difficult both because the EP components tend to be inherently variable and because they have to be extracted from the extremely variable and often larger SP.

The superposition or averaging of a sequence of measured waveforms time-locked to repeated stimuli is used in an effort to emphasize the relatively stable EP components therein and de-emphasize the more variable SP components. Traditionally, the clinician relies on visual inspection of averaged waveforms in seeking to extract the relevant diagnostic features from a highly complex waveshape. The accuracy of the procedure depends to a great extent on the experience, skill and judgment of the particular clinician, and is immensely complicated by the high inherent variability of the relevant traces. Although this variability is largely due to ongoing physiological processes generating brain electrical activity, it is unrelated to the effects of the stimuli, and will be referred to as "noise" hereafter. It is highly desirable in certain cases simply to detect the presence of an evoked response in averaged waveforms. One simple example is when a need exists to known if the brain of a patient who is unable or unwilling to provide reliable subjective information shows an electrical response to sensory stimuli—for example in the case of a comatose or an anesthetized patient, a person with psychological impairments, an infant, or an uncooperative patient. It has been proposed in the past that the presence or absence of a significant brainstem evoked potential can be determined by finding the difference in spectral power between a patient's averaged waveforms in the absence and in the presence of an auditory stimulus, and comparing the difference with that recorded for a large population of previously tested "normal" subjects. In particular, it has been proposed to average a succession of 2,000 segments of a patient's brainwave signal in the absence of an auditory stimulus and another succession of 2,000 equally long segments time-locked to the presentation of an auditory stimulus, and to compare the difference in the spectral power of the two averages with the corresponding difference for a large population of normally functioning subjects known or believed to have responded in a certain way to a similar stimulus. See, for example, Laukli, E., et al., Early Auditory-Evoked Responses: Spectral Content, Audiology 20: 453–464 (1981). See, also, for background information, John, E. R., et al., Neurometrics, Science, Vol. 196, pp. 1393–1410, June 24, 1977 and U.S. Pat. Nos. 4,279,258; 4,201,224; 4,216,781; 4,188,956; 4,171,696; 3,901,215; 3,780,724; 3,705,297 and 3,696,808. As an example of a proposal for Fourier transform spectrum evaluations in connection with electroencephalography, see U.S. Pat. No. 3,725,690.

Despite the known efforts made in the prior art toward accurately detecting and interpreting EP, it is believed that much need remains for improvements which would make averaged waveforms evaluation more reliable and useful even in the absence of highly trained interpretation experts, and would reduce the incidence of false positive and false negative results. Accordingly, one object of the invention is to provide a method and a system for determining the presence of significant evoked potential in brainwaves, through an automated test which reduces the likelihood of subjective errors. Another is to carry out such test in a manner which tends to reduce the incidence of false positive and false negative results by departing from the known prior art and using primarily the brainwaves of a particular patient to determine how much of a difference between them in the absence and in the presence of a stimulus would be sufficient to indicate the presence of a significant evoked potential. Yet another is to determine the presence of a significant evoked potential in a manner which allows quantification of the likelihood that the results would be accurate for the particular patient being tested. Yet another is to end the test as soon as a sufficiently unambiguous determination has been made, and to end the test in any event if undue doubt still remains after a certain number of attempts.

In a specific and nonlimiting example of the invention, as applied to testing for the presence of significant evoked potential, a first set of averaged waveforms is derived from a patient in the absence of the selected stimulus and a second set of averaged waveforms is derived from the same patient in the presence of the stimulus. Respective spectral measures are found for the averaged waveforms when the stimulus is absent and a similar spectral measure is found for the corresponding averaged waveforms when the stimulus is present. The two sets of spectral measures are used to produce a test measure which reflects the difference between the mean values of the two sets of spectral measures in respect to their variance. This test measure is matched against an acceptance level and a rejection level, which in turn are functions of the number of averaged waveforms which go into finding the spectral power measures, and also reflect the desired degree of likelihood that the end result will be accurate for the particular patient under test. If the presence or absence of a significant evoked potential can be determined at this time sufficiently unambiguously, the end result is displayed and the test ends. Otherwise, the test goes on to process additional alterante sequences of averaged waveforms, one dervied in the presence and the other in the absence of the stimulus, until either (i) the presence or the absence of a significant evoked potential can be determined sufficiently unambiguously or (ii) a maximum allowable number of such sequences has been processed as described. In one example the stimulus is auditory; in another it is a skin electric shock (or any other stimulus useful for testing sensory pathways).

DETAILED DESCRIPTION

Figure 1:
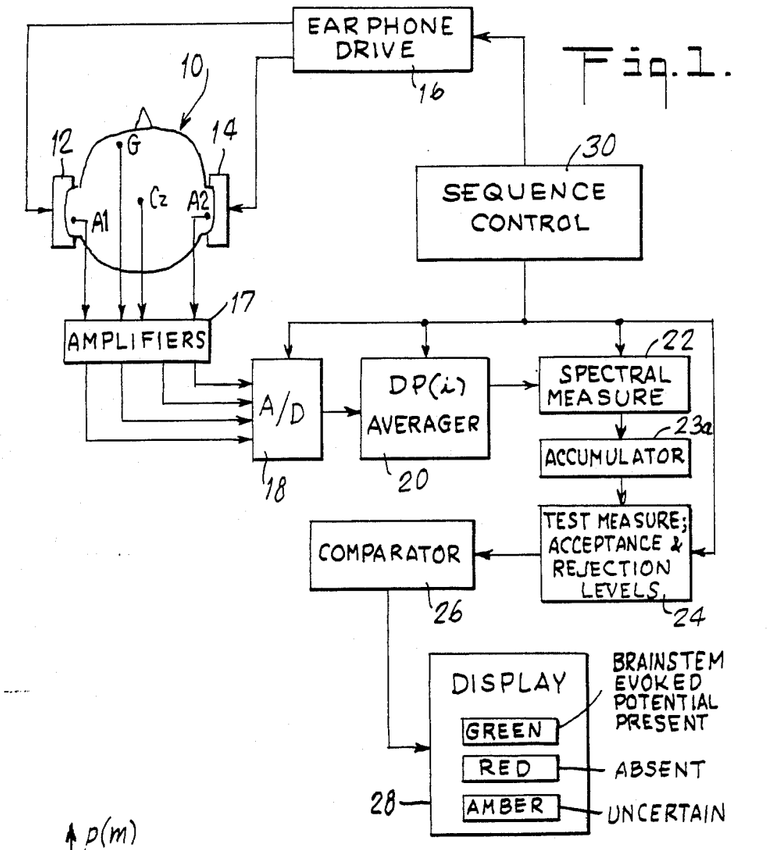
FIG. 1 is a partly schematic and a partly block diagram of a system embodying an example of the invention.

Referring to FIG. 1 for an illustration of a system embodying an example of the invention as applied to testing for the presence of a significant brainstem evoked potential in response to an auditory stimulus, a patient 10 has scalp electrodes G and Cz, and earlobe electrodes A1 and A2 at the indicated positions of the international 10-20 system. Cz is the active electrode, A1 and A2 serve as reference electrodes and G as the ground electrode. Earphones 12 and 14 are over the patient's left and right ears respectively, and are selectively energized by earphone drive 16 to provide an auditory stimulus, e.g., clicks at a selected volume level and at a selected rate. The outputs of electrodes A1, A2 and Cz are amplified at 17 relative to the potential of the ground electrode G, and the respective amplified outputs are supplied to an analog-to-digital converter 18, which selectively samples them to produce respective digital samples. In the example of testing the response to an auditory stimulus applied to the right ear, the signal of interest is the output of electrode Cz with respect to the reference electrode A1 on the left earlobe. Conversely, when the stimulus is applied to the left ear, the signal of interest is the output of electrode Cz relative to A2. Examples of the types of measured waveforms derived from electrode Cz, relative to A1 (or A2), in the absence and presence of an auditory stimulus are illustrated in FIGS. 2A–2H on a voltage vs. time plot, together with an exemplary waveform of the auditory stimulus click on a αB vs. time plot. Referring again to FIG. 1, A/D converter 18 samples the relevant signal (e.g., Cz relative to A1) to produce a sequence of digital samples, e.g., at a rate of 10,000 samples per second.

In one nonlimiting example of a test sequence, at first there is no auditory stimulus, and the output of electrode Cz relative to A1 is a first measured waveform produced in the absence of a stimulus. In order to start collecting measurements for use in deriving a spectral measure of the averaged waveform in the absence of the stimulus, A/D unit 18 takes a sample DP(i) of this first measured waveform every one hundred microseconds, and supplies a sequence of 128 successive samples (said sequence being called an epoch herein) to averager 20, which I=128 storage locations each storing a respective 12-bit sample DP(i). For the next measured waveform in the absence of the stimulus, the next epoch of samples DP(i) from A/D unit 18 is added in averager 20 by sample position to the previously stored one, i.e., sample DP(1) from the second epoch is added to sample DP(1) of the first epoch and the result is stored in the first position in averager 20, sample DP(2) of the second epoch is added to sample DP(2) of the first one and the result is stored in the second position in averager 20, etc. This process continues until a group of two hundred successive epochs has been so accumulated in averager 20. Averager 20 now divides the contents DP(i,acc.) of each sample position by the number of accumulated epochs N=200, and stores the result DP(i) in the same sample position, i.e.:

$$DP(i) = (1/N)DP(i,acc.) \qquad (1)$$

Figure 2A:
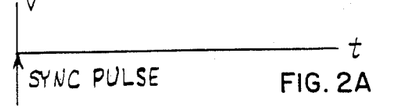
FIGS. 2A–2H illustrate a synchronization pulse, an auditory stimulus, a spontaneous and an evoked potential measured waveform, superpositions of spontaneous and evoked potential waveforms, and respective averaged waveforms in the absence and in the presence of the stimulus.
Figure 2B:
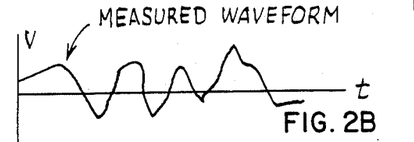
Figures 2C, 2G:
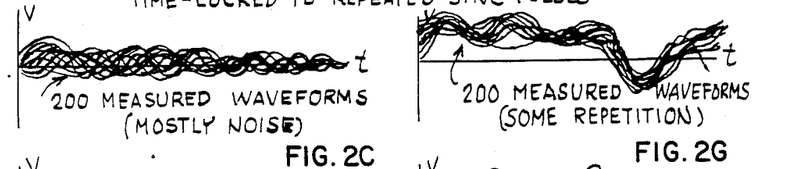
Figures 2D, 2H:
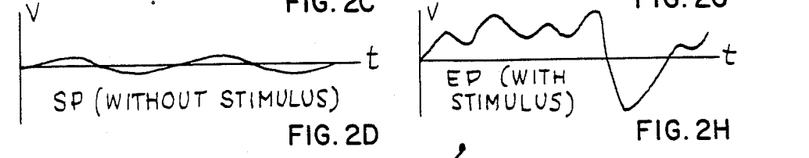
Figure 2E:
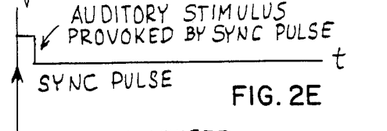
Figure 2F:
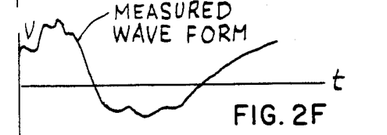

At this time, averager 20 contains, in digital sample form, a first averaged waveform derived from a group K (at this time K=1) of N=200 epochs (measured waveforms) in the absence of the auditory stimulus. This averaging process, resulting in an averaged waveform of the type illustrated in FIG. 2, helps reduce at least some of the undesirable effects of the random noise on the measured waveforms.

In order to find a spectral measure of the averaged waveform (stored in digital form in unit 20) unit 22 now subjects it to Fourier transformation to derive 64 pairs of Fourier coefficients a(m) and b(m), where m=1,2,...,64, for example by using a known process described by:

$$a(m) = (1/I) \sum_{i=1}^{I} DP(i) \cos(2\pi m\, i/I) \qquad (2)$$

$$b(m) = (1/I) \sum_{i=1}^{I} DP(i) \sin(2\pi m\, i/I)$$

where the summation is over the sample index i which varies from 1 to I=128. The spectral measure P(K) for the current group K of N=200 epochs is then found as the sum of the logarithms (to base 10) of the spectral power values p(m) of a selected subset of Fourier series components by a process described by:

$$P(K) = \sum_{m(\text{selected})} \log_{10} p(m) \qquad (3)$$

where the spectral power p(m) of each respective pair of selected Fourier series component identified by the respective index m is found through a process described by:

$$p(m) = (\tfrac{1}{2})[a^2(m) + b^2(m)] \qquad (4)$$

While it is possible to use the spectral powers p(m) of all 64 Fourier series components in finding the spectral measure P(K), it has been discovered in making this invention that markedly superior results are obtained if a selected subset thereof is used. This subset is comprised of the components identified by the indices m for which the spectral powers p(m) for the presence and absence of the auditory stimulus tend to differ from each other more than for non-selected indices m, for which they tend not to differ from each other. In effect, the contribution of "noise" to the average waveforms computed in the presence and absence of the stimulus is substantially represented by the components corresponding to the non-selected indices, while the contribution of signal is primarily described by the selected indices.

At this time, the system has processed the first N=200 epochs (measured waveforms) in the absence of the auditory stimulus, and has found the spectral measure P(K) for K=1. Thereafter, in order to start collecting measurements for use in deriving a spectral power measure of the first averaged waveform in the presence of the stimulus, earphone drive 16 energizes earphone 14 to produce a stimulus in the form of a succession of clicks, spaced in time from each other to allow a measured waveform to be derived from electrode Cz (referenced to A1) in synchronization with each click, as illustrated in FIGS. 2A-2H. A/D unit 18 now samples this succession of measured waveforms in the presence of the stimulus in the same manner, and delivers to averager 20 similar epochs, each made up of a succession of 128 digital samples DP(i) and each commencing with the onset of a click generated by earphone 14. After N=200 such measured waveforms (epochs) in the presence of the stimulus are accumulated, they are averaged in accordance with the process defined by expression (1) to store in averager 20 I=128 samples DP(i) of the first averaged waveform in the presence of the stimulus (for K=1). This averaged waveform is now processed in unit 22 to find the spectral measure P'(K) for, at this time, K=1, using the same process as discussed above for finding P(K). This derivation of the spectral measures P(K) and P'(K) for two averaged waveforms, one in the absence and the other in the presence of the stimulus, completes one acquisition cycle K (at this time K=1).

Figure 3:
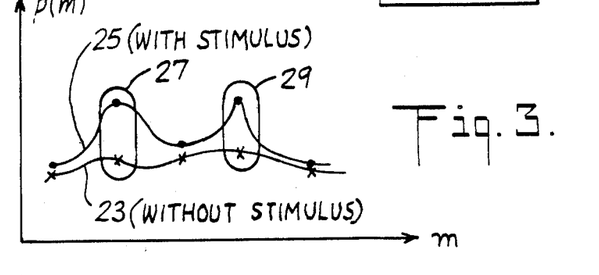
FIG. 3 illustrates spectral measures relating to averaged waveforms in the absence and in the presence of a stimulus.

Returning to the selection of coefficients for use in finding the spectral measures P(K) and P'(K), refer to FIG. 3 and suppose that curve 23 connects spectral power values p(m) for the absence of the stimulus and curve 25 connects corresponding spectral power values p(m) for the presence of the stimulus. Five pairs of p(m) and p'(m) points are illustrated, and it is apparent that the difference in value between the points of pairs 27 and 29 is much greater than that for the other three pairs. In accordance with the invention, only six pairs of spectral measure values p(m) and p'(m), each found as described by expression (4), are used in finding the spectral measure P(K) (or P'(K)), selected such that the difference between the spectral powers p(m) and p'(m) in a selected pair tends to be more than for the remaining 58 pairs. In accordance with the invention, the six pairs of spectral power values which are likely to be most useful are identified by testing a large population of subjects to find the 64 pairs of spectral power values p(m) and p'(m) for each subject in the absence and in the presence of the stimulus, obtaining the mean value and the standard deviation for each of the 64 spectral power values in the population of subjects for both conditions of absence and presence of the stimulus, calculating a t-test statistic (a known statistical test for determining the significance of the difference between the means of two groups of values) for each of the 64 pairs of means of spectral power values for the population and selecting the spectral power values which tend to exhibit the greatest values of the t-test statistic. In a particular example of practicing the invention, the following spectral power values p(m) and P'(m), identified by their index m, are used: 4, 6, 7, 11, 12, 13. The corresponding frequencies in Hz are: 320, 480, 560, 880, 960, 1040. Of course, since only six pairs of spectral power values, each value derived from a pair of Fourier series coefficients, are needed in this example of the invention for a particular pair of spectral measures P(K) and P'(K), no time and effort need be spent on finding the remaining 58 pairs of spectral power values and 116 pairs of Fourier series coefficients.

The difference between the two spectral measures P(K) and P'(K) for K=1, i.e. after the first acquisition cycle, is not believed to be by itself a reliable indicator of the presence or absence of brainstem evoked potential. Such difference can be due, for example, to random factors in the spontaneous potential and/or to pure noise. In order to find differences which in accordance with the invention are much more likely to be significant and reliable indicators of the absence or presence of significant evoked potential, additional acquisition cycles are carried out, to derive additional pairs of spectral measures P(K) and P'(K), for K=2,3, etc., and the so derived spectral power measures are in turn used to derive a test measure which reflects both (i) the difference between the averages of the spectral measures for the two conditions (absence and presence of the stimulus) and (ii) the variance of the spectral measures P(K) and P'(K) for the subject being tested.

Specifically, a test measure V(K) is derived from quantities designated A, A', S and S', which in turn are accumulated from the spectral measures P(K) and P'(K) derived in the K acquisition cycles. In particular, the spectral measures P(1) and P'(1) are found as described for the first group k of digital samples (for K=1), and are stored in locations A and A' respectively in accumulator 23a. In addition, the squares of the same spectral measures are stored in locations S and S' respectively in the same accumulator 23a. Then averager 20 is cleared, and the system of FIG. 1 commences the same process for a subsequent group of digital samples (for K=2) to thereby produce spectral measures P(2) and P'(2). The spectral measures P(2) and P'(2) and their respective squares are added to the contents of locations A, A', S and S', respectively, of accumulator 23a. As this process is repeated K times, unit 23a accumulates the spectral measured P(k) for K averaged waveforms to thereby derive, for the absence of the stimulus, a statistic A described by:

$$A = \sum_{k=1}^{K} P(k) \tag{5}$$

and similarly derives a corresponding statistic A' for the averaged waveforms in the presence of the stimulus. In addition, unit 23a accumulates the squares of the spectral measures P(k) for the K groups of averaged waveforms in the absence of a stimulus, to thereby derive a statistic S described by:

$$S = \sum_{k=1}^{K} [P(k)]^2 \tag{6}$$

and similarly derives a corresponding statistic S' for the averaged waveforms in the presence of the stimulus.

By now the system has made use of K groups of digital samples for respective intervals of the measured waveforms derived from the patient in the absence and in the presence of the stimulus, and has produced therefrom statistics A, A', S and S'.

After the system completes in this manner K=K(min) acquisition cycles, it uses those statistics to derive the sought test measure V(K) which, as earlier, noted, reflects not only the difference between mean spectral measures of the averaged waveforms in the absence and in the presence of the stimulus but also how significant this difference is with reference to the variance of those spectral measures for the particular subject being tested. A particularly important consequence of this feature of the invention is that the averaged waveforms from the individual patient under test are used to evaluate the significance of the measured difference between that patient's measured brain waveforms in the absence and in the presence of the stimulus. This is in contrast with the known prior art, in which the measured difference between corresponding averaged waveforms is tested, at least a principle, against a similar difference found a priori for a large number of subjects presumed to exhibit normal brainstem evoked potentials in similar circumstances. This aspect of the invention thereby contributes to accounting for the uniqueness of the measurement conditions prevailing when deriving the relevant signals from the individual patient under test, and is believed to contribute significantly to reducing the incidence of false positive and false negative end results.

An example of a test measure V(K) making use of this aspect of the invention is defined by:

$$V(K) = (A' - A)/[2K(S' - S) - (A' - A)^2]^{\frac{1}{2}} \quad (7)$$

and is generated in unit 24 from the statistics A, A', S and S' accumulated in unit 23a and the number K of pairs of averaged waveforms used in producing said statistics.

In order to determine if the test measure V(K) corresponds to the presence or the absence of a significant evoked potential (or perhaps is such that the presence or absence of said potential cannot be determined with sufficient certainty), unit 24 generates an acceptance level signal Va(K) and a rejection level signal Vr(K). In accordance with another important aspect of the invention, the levels Va(K) and Vr(K) take into account the particular measurement conditions, and are determined on the basis of (i) the number of pairs K of averaged waveforms which go into finding the test measure V(K), (ii) a selected degree of risk that the system will indicate the presence of a significant evoked potential when in fact it is absent, and (iii) a selected degree of risk that the system will indicate the absence of the evoked potential when it is in fact present. These selected, allowable risks are designated (i) "alpha," which is the probability of the system detecting the presence of a significant evoked potential when it is in fact absent, and (ii) "beta," which is the probability of the system detecting the absence of a significant evoked potential when it is in fact present. In a particular, nonlimiting example of the invention, the acceptance level Va(K) and rejection level Vr(K) are found from the following relationships (8) and (9) whose solution can be obtained from "Tables to Facilitate Sequential t-Test," U.S.A. National Bureau of Standards, Applied Mathematics Series, 7, 1951, and in which "delta" is a relative sensitivity level:

$$e - (K\delta^2/2) \sum_{j=0}^{\infty} (K - 2 + j)![K\delta^2 Va(K)^2]^j / (K - 2)!(2j)! = \quad (8)$$

$$1 - 2\beta)/2$$

-continued $$e - (K\delta^2/2) \sum_{j=0}^{\infty} (K - 2 + j)![K\delta^2 Vr(K)^2]^j / (K - 2)!(2j)! = \quad (9)$$

$$2\beta/(1 - 2\alpha)$$

As one example, alpha and beta can each be set to 0.05 and delta can be set to unity. K in expressions (8) and (9) is the number of pairs of averaged waveforms have been used in finding the spectral power statistics which have gone into finding the test measure V(K). The levels Va(K) and Vr(K) can be found as described for each of the expected values of K a priori (e.g., from K=K(min)=6 to K=K(max)=40), and stored in unit 24 so as to avoid the need to calculate them anew each time they are needed.

In order to determine the significance of the test measure V(K) for the particular patient being tested, the system compares it with the levels Va(K) and Vr(K) in unit 26. If V(K) is found to be greater than or equal to the acceptance level Va(K), unit 26 generates a signal indicative of the likely presence of a significant evoked potential in the patient being tested, and this signal is supplied to display unit 28 to energize a normally OFF green indicator thereof, which can have an appropriate label and to turn OFF a normally ON amber indicator. A normally OFF red indicator in unit 28 remains OFF at this time, as it is energized only when the system determines that it is likely that a significant evoked potential is absent. The normally ON amber indicator lights up as soon as the system is first turned ON and remains energized, to indicate uncertainty as to the presence or absence of said evoked potential, for as long as none of the green and red indicators is energized. If after processing the minimum selected number K(min) of groups of digital samples comparator 26 determines that V(K) is less than or equal to the rejection level Vr(K), it applies a corresponding signal to display 28 to turn ON the red indicator thereof and de-energize the amber indicator.

In case these tests shown that V(K) is less than Va(K) but greater than Vr(K), the amber indicator remains energized, as this means that the groups K processed so far cannot give a sufficiently unambiguous end result. In such a case, the system continues seeking under the direction of sequence control 30 by deriving and processing anothr pair K of averaged waveforms represented as digital samples (for K=7). If the amber indicator at display 28 still remains ON, the system keeps repeating the same process until one of two end results: (i) the output of comparator 26 turns ON either the green or the red indicator at display 28 (and turns OFF the amber indicator), or (ii) the system has processed a selected maximum number of groups K=K(max) of digital samples (e.g., K(max)=40). Of course, the spectral measures P(K) and P'(K) are derived and the statistics A, A', S and S' are updated each time the index K is incremented to a new value K.

Figure 4:
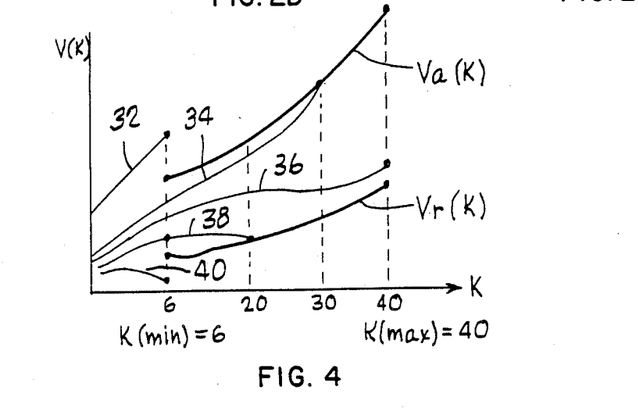
FIG. 4 illustrates the relationship between possible test measures and acceptance and rejection levels.

Referring to FIG. 4 for an illustration of the test measure V(K) as compared to the acceptance and rejection levels Va(K) and Vr(K), suppose the acceptance and rejection levels vary with the number K of pairs of averaged waveforms between K(min)=6 and K(max)=40, as indicated by the respective curves. Suppose, as a first example, that the test measure V(K) varies with the numbers of pairs K used in deriving it, as illustrated by curve 32; in such a case the system of FIG. 1 will indicate the likely presence of a significant evoked potential as soon as the sixth pair of averaged waveforms is processed. As another example, suppose the test measure V(K) varies as indicated by curve 40 in FIG. 4; in such a case the system will indicate the likely absence of a significant evoked potential as soon as the sixth pair of averaged waveforms is processed as described. Suppose as yet another example that the test measure varies as indicated by curve 34 in FIG. 4; in such a case, the test measure V(K) remains in the uncertainty zone between the acceptance and the rejection level curves at k=6, and the system will continue processing additional pairs K of averaged waveforms until curve 34 crosses the acceptance level curve at K=30, and will at that time indicate the likely presence of a significant evoked potential. Suppose, as yet another example, that the test measure V(K) varies as indicated by curve 36 in FIG. 4, and remains in the uncertainty zone between the acceptance and rejection levels for the entire range through K=40; in such a case the system will stop after the 40th pair of averaged waveforms and the amber indicator of display 28 will remain ON, to indicate that it is uncertain whether a significant evoked potential is present or absent. Suppose, as a last example, that the test measure varies as curve 38 in FIG. 4; in such a case the system will continue processing averaged waveform pairs 7,8, etc. until curve 38 crosses the rejection curve at k=20, at which time display 28 of FIG. 1 will turn ON the red "absent" indicator and de-energize the amber "uncertain" indicator, to show the likely absence of a significant evoked potential.

The system of FIG. 1 can be implemented as a completely hard-wired or firm-wired system, using commercially available components interconnected and arranged as taught herein to implement the new combination of functions. As one example, unit 16 can be a commercially available audio generator capable of causing earphones 12 and/or 14 generate an auditory stimulus in the form of a succession of clicks, each having a hundred microseconds duration at a selected level of, e.g., 10–75 db above white noise at a selected level of, e.g., 40–70 db. Amplifier 17 can comprise, for each electrode, a respective commercially available, high quality, low-noise amplifier suitable for very low input voltage and power, and A/D unit 18 can be a commercially available 12-bit converter capable of selecting the appropriate lead from amplifiers 17 and coupled with a suitable sampling circuit for operating at a rate of 10,000 samples per second. Averager 20 and accumulator 23a can make use of a suitable partitioned area in the memory of a general purpose digital computer, or can comprise dedicated bitslice circuits. Unit 22 can be a commercially available FFT processor, or can be implemented by means of a general purpose digital computer programmed and arranged to carry out the operations described herein in deriving and evaluating the spectral measures P(K) and P'(K). Unit 24 can be a hard- or firm-wired circuit for deriving and storing the test measure and the acceptance and rejection levels discussed above, or can be a general purpose digital computer programmed and arranged, as taught herein, to carry out the relevant operations. Comparator 26 can be a commercially available digital comparator carrying out the relevant functions described herein, or can be a general purpose digital computer programmed and arranged, as taught herein, to carry out the indicated comparisons. Display 28 can be a commercially available display having three energizable indicators, or can be a specially made device capable of carrying out the operations described herein. Alternately, the elements 20, 22, 23, 24, 26 and 30 (FIG. 1) can be implemented by means of a general purpose computer system programmed to carry out the process described above. As the memory capacity and other requirements of the process are relatively modest, such computer system can be relatively small, down to the size of the smaller commercially available microcomputers or the commercially available microprocessor-based system.

Figure 5A:
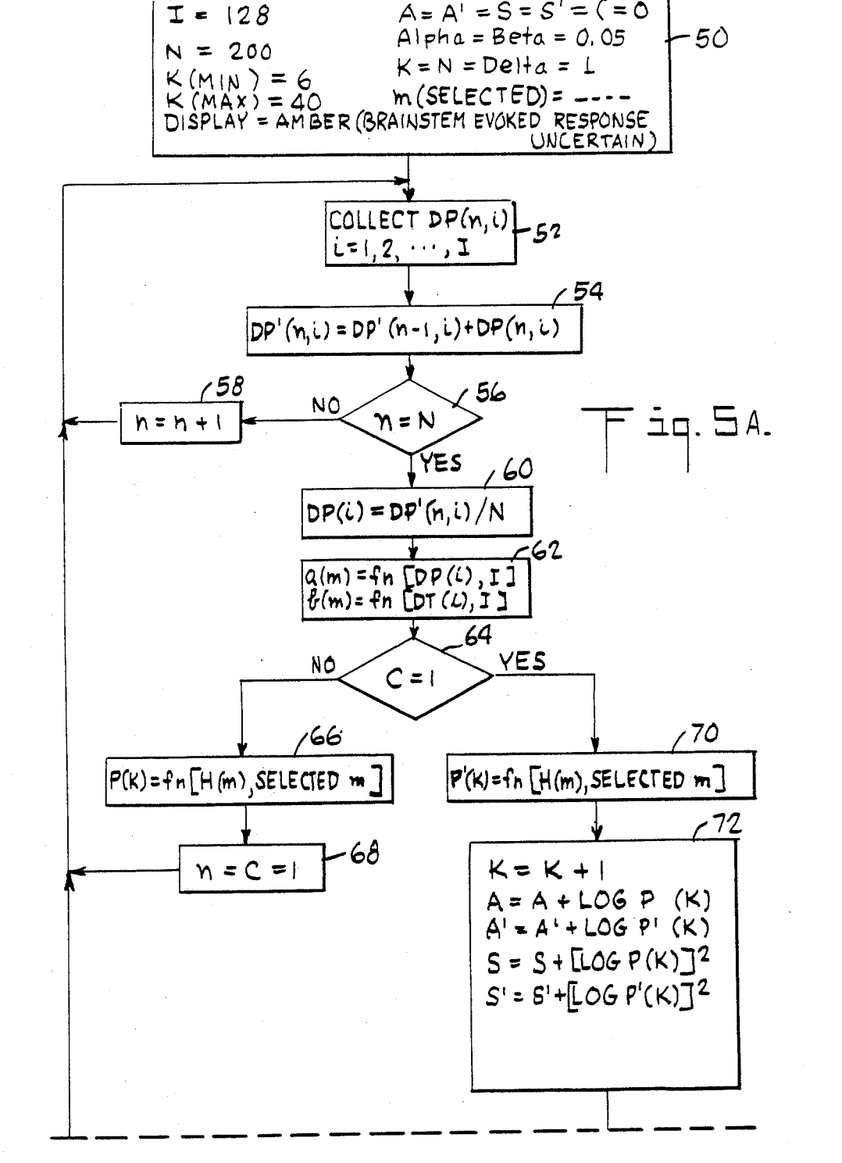
FIGS. 5a and 5b comprise a flowchart of a process embodying an example of the invention.
Figure 5B:
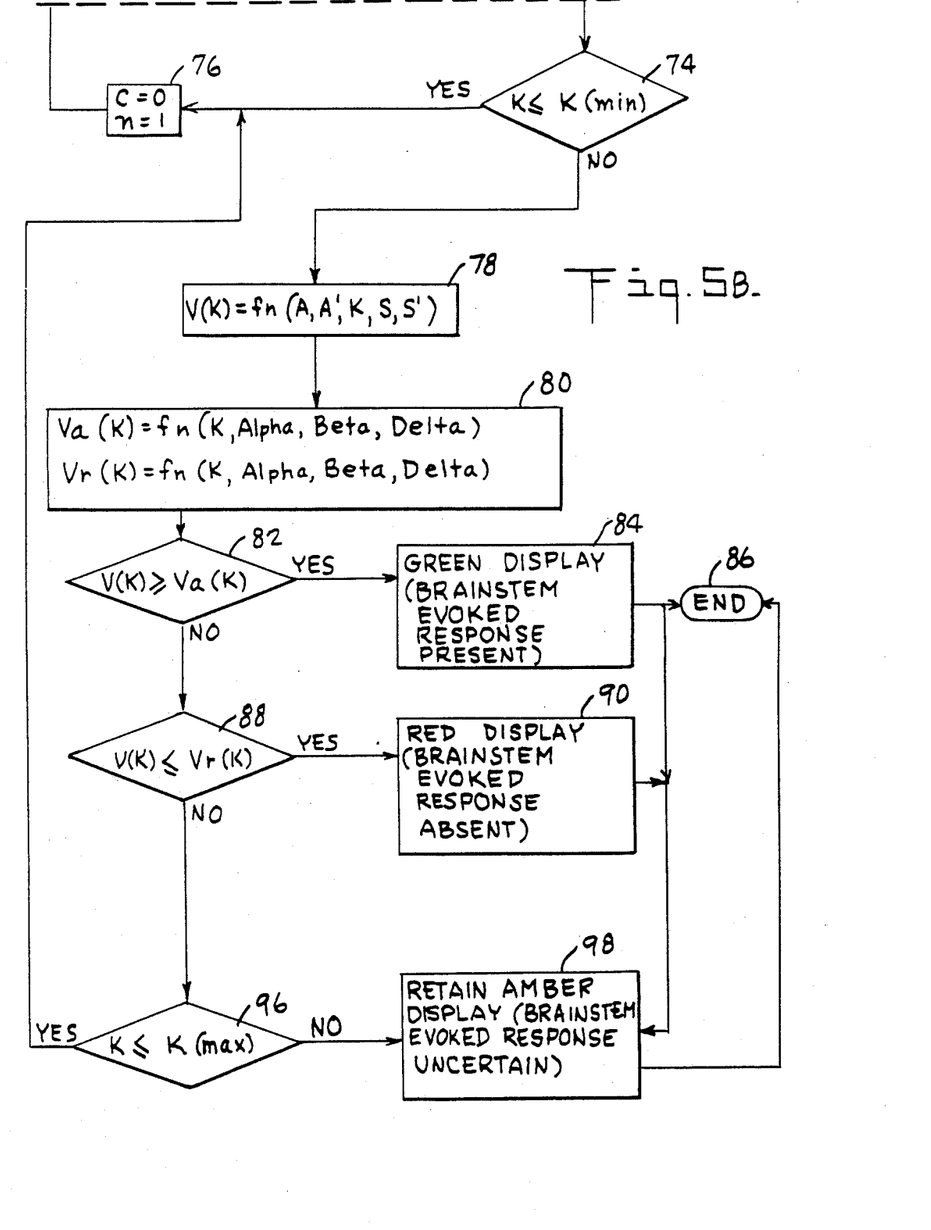

A detailed flowchart of the process carried out by the system of FIG. 1 is illustrated in FIGS. 5a and 5b, which can be used either as a guide to building a hard- or firm-wired system, or as a guide to programming a selected general purpose digital computer system. In order to make the description more concise, as well as more easily understood, no specific formal computer language is used, but it should be apparent to those skilled in the art that each of the steps illustrated in FIG. 5 and described herein is easily translatable to one or a few statements of a selected computer language.

Referring to FIG. 5, step 50 is the selection of initial parameters: there will be I=128 digital samples DP(i) of the relevant brainwave signal in each epoch, there will be N=200 epochs of samples of each of the two relevant measured brain waveforms in a group, the minimum number K(min) of pairs of averaged waveforms will be 6 and the maximum K(max) will be 40, each of the statistics A, A', S, S' and C is initially set to zero, each of the parameters alpha and beta is set at 0.05, each of the parameters K and delta is set to unity, the selected Fourier series coefficients used in spectral power derivation are those identified by the indicated indices m, and the display is set to energize its amber indicator (standing for an indication that it is uncertain whether or not the patient being tested has a significant evoked potential). Of course, other choices of initial parameters can be made within the scope of the invention. For example, a different number of samples, e.g., 64, can make up an epoch (a measured waveform), a different number of epochs can make up an averaged waveform, different minimum and maximum numbers of pairs of averaged waveforms can be selected, different probability levels can be chosen for alpha and beta, and alpha and beta can be different from each other. Similarly a different value can be selected for delta, and different selected indices m can be chosen or, alternately, all of the Fourier series coefficients can be assessed in selecting the relevant spectral powers.

At step 52, the process starts collecting the digital samples DP(i) produced from A/D unit 18 in FIG. 1 from the measured brain waveforms, in the absence of the auditory stimulus. Note that the parameters C were set to zero in step 50 to indicate that the initial samples are for the case when the auditory stimulus is absent. After a total of I successive samples have been collected at step 52 to make up the first epoch (for n=1), step 54 runs in sequence through the indices i to accumulate the respective digital samples. The accumulation of samples DP(i) for a given position i in the epoch is designated DP'(n,i), where n designates the position of the epoch n in the group of a total of N epochs. Of course, for the first run through step 54, the previous accumulation DP'(n−1,i) is zero. After the accumulations at step 54, step 56 checks if the current epoch is the last one of the group of N; if the answer is negative, step 58 increments the epoch index n and the process returns to step 52 to start collecting the digital samples for the next epoch.

When step 56 indicates that the last of the N epochs has been collected and accumulated, step 60 finds the average DP(i) of each respective digital sample position by dividing the respective accumulated value DP'(N,i) by the number of epochs N, and step 62 uses the averaged digital sampls DP(i) to find the required Fourier series coefficients a(m) and b(m) as a function thereof, for example by the use of the relationship therebetween represented by expressions (2). Step 64 then checks if parameter C is unity—if it is not, as is the case now because the system has so far been working with samples of the brainwave in the absence of the auditory stimulus, the system goes to step 66 to find the spectral measure P(K) for the current pair of averaged waveforms. For the first run through step 66, K is, of course, unity. P(K) preferably is found by using only the coefficients identified by the subscripts M selected at step 50, as discussed in connection with expresions (3) and (4).

In order to now process the brainwave signal derived in the presence of the auditory stimulus for the current pair K of averaged waveforms, at step 68 the system sets parameter C to unity, sets the index n to one to start with the first epoch thereof, and then returns to step 52. This time, when the process reaches step 64 the result is positive and the process goes to step 70, to find the spectral measure P'(K). Now that both of the necessary spectral measures have been found for the current pair K, step 72 increments the K to identify the next pair, and updates the statistics A, A', S and S'' as indicated. Step 74 then checks if the updated index K still identifies a pair within the limit K(min) and, if the test yields a positive result, step 76 sets the parameters C to zero, to identify the measured response waveform in the absence of the stimulus, and sets the index n to one to start collecting the first epoch of the current pair K. The process then again returns to step 52.

When the tested step 74 indicates that all of the averaged waveforms within K=K(min) have been processed, step 78 finds the test measure V(K) as a function of the statistics updated in step 72, as described in connection with expression (7), and step 80 finds the acceptance and rejection levels Va(K) and Vr(K) as respective functions of the index K updated in step 72 and the parameters alpha, beta and delta set in step 50. Note that the relevant levels of Va(K) and Vr(K) for each K in the range of 6 through 40 can be found in tables in said National Bureau of Standards book, and stored in a look-up table which can be used instead of solving expressions (8) and (9) each time an answer is necessary.

Once the test measure V(K) is available from test 78 and the acceptance and rejection levels Va(K) and Vr(K) are available from step 80, a test is made at step 82 to determine if the test measure is greater than or equal to the acceptance level. A positive result means that it is likely that a significant evoked potential is present, a green display is activated at step 84 to indicate this determination (and the amber display at step 98 is turned OFF), and the process ends at step 86. In case of a negative result in step 82, a test is made at step 88 to determine if the test measure is less than or equal to the rejection level. In case of a positive result, a red display is energized at step 90 to indicate that it is likely that a signicant brainstem evoked response is absent, and the amber display at step 98 is turned OFF and the process ends at step 86. A negative result indicates that it is still uncertain whether it is likely that a significant evoked potential is present or absent, and a test is made at step 96 to determine if the index K identifies a pair of averaged waveforms within the maximum allowable number of 40 pairs. In case of a positive answer at step 96, the process returns to step 76, to set C to zero and thus identify the measured waveforms in the absence of the stimulus, and to set the index n to 1 and thus identify the first epoch to be processed. In case of a negative answer at step 96, meaning that there is still uncertainty after all of the 40 pairs of averaged waveforms have been processed, step 98 retains the amber display, and the process ends at step 86.

The particular, nonlimiting example of the invention described above involves the use of an stimulus to test the brainstem evoked potential, but it should be clear that the teachings herein of a process and system apply in the case of an electrical tactile stimulus, or a visual, auditory or somatosensory critical evoked response, which require an analysis from 100 to 500 ms depending upon the particular clinical application. Of course, in such a case earphone drive 16 in FIG. 1 will be replaced by a drive for electrical shock electrodes or for visual stimulators, earphones 12 and 14 will be replaced by appropriate tactile electrical stimulus electrodes applied to the patient's body or visual stimulators and the scalp electrodes will be placed at positions appropriate for the detection of evoked potentials believed to be associated with electrical tactile or visual stimuli. It shoulde also be noted that these teachings are not limited to brainstem evoked potential, but apply to cortical evoked potentials as well, and that this specification will teach those skilled in the art many variations of the exemplary process and system described in detail above as applicants' best mode, and that such variations will be within the scope of the invention, which is defined by the appended claims.

We claim:
1. A machine-implemented method comprising:
deriving for the same patient a first set of averaged brain waveforms in the absence of a stimulus and a second set in the presence thereof;
seeking a test measure related to averaged spectral characteristics of the first and second sets of averaged brain waveforms and to their variance; and
evaluating the test measure relative to one or more levels determined as a function of the number of averaged brain waveforms to ascertain the likelihood that the patient exhibited or failed to exhibit a significant evoked potential in response to said stimulus.

2. A method as in claim 1 in which said deriving, seeking and evaluating steps are carried out for a first and a second set each having a minimum selected number of averaged waveforms and, if the evaluating step does not ascertain said likelihood sufficiently unambiguously, repeating the deriving, seeking and evaluating steps for sets having successively greater numbers of averaged waveforms until the evaluating step ascertains said likelihood sufficiently unambiguously, but ending said repetition upon said sets having been expanded to a selected maximum number of averaged waveforms.

3. A method as in claim 1 in which the seeking step comprises finding a test measure related both to the difference in mean values between spectral characteristics of the first and second sets of averaged brain waveforms and to the variance of said spectral characteristics.

4. A method as in claim 1, 2 or 3 in which the seeking step comprises finding the logarithm of the spectal power of each averaged waveform using only selected coefficients of a Fourier series representation of the respective waveform, finding the difference between the respective accumulations of the power spectra of the second and first sets of averaged waveforms and dividing said difference by a variance measure thereof.

5. A method as in claim 4 in which said selected Fourier series coefficients are those which have been found most likely to differ as between the presence and absence of the stimulus for a large population of subjects believed to exhibit a significant evoked potential in response to said stimulus.

6. A method as in claim 1, 2 or 3 in which the evaluating step comprises evaluating relative to a rejection level and an acceptance level, said levels being determined on the basis of: the number of averaged waveforms in said sets, a selected degree of risk that the testing step will ascertain the likely presence of a significant evoked potential, when in fact it is absent, and a selected degree of risk that the testing step will ascertain the likely absence of a significant evoked potential, when in fact it is present.

7. A method as in claim 1, 2 or 3 in which said stimulus is an auditory stimulus.

8. A method as in claim 1, 2 or 3 in which the stimulus is selected from the group consisting of auditory, visual and somatosensory stimuli.

9. A method as in claim 7, in which said evoked potential is indicative of a brainstem response to the stimulus.

10. A method comprising deriving a first and a second set of a subject's averaged brain waveforms, one in the absence and the other in the presence of a stimulus, finding therefrom a test measure of the discrepancy therebetween, and ascertaining, on the basis of spectral characteristics of the averaged waveforms rather than only the number of waveforms which have been averaged, whether the subject exhibits a significant evoked potential in response to the stimulus to a predetermined risk of false positive and false negative results.

11. A system comprising:
means for deriving for the same subject a first set of averaged brain waveforms in the absence of a stimulus and a second set in the presence thereof;
means for seeking a test measure related to averaged spectral characteristics of the first and second sets of averaged brain waveforms and to their variance; and
means for testing the test measure relative to one or more levels determined as a function of the number of averaged brain waveforms to ascertain the likelihood that the subject exhibited or failed to exhibit a significant evoked potential in response to the stimulus.

12. A system as in claim 11 including means operative if the testing means fail to ascertain said likelihood sufficiently unambiguously for a minimum selected number of averaged waveforms, to successively increase the number of averaged waveforms in a set until the testing means can ascertain said likelihood sufficiently unambiguously or until the sets comprise a maximum number of averaged waveforms, whichever comes first.

13. A system as in claim 11 in which the seeking means comprise means for finding said test measure as a function of both the difference in mean values between spectral characteristics of the first and second sets of averaged waveforms and to a measure of the variance of said spectral characteristics.

14. A system as in claim 11, 12 or 13 in which the seeking means comprise means for finding the logarithm of a spectral power measure of each averaged waveform, finding the difference between the respective accumulations of said logarithms for the second and first sets of averaged waveforms and dividing the difference by a variance measure of said spectral powers.

15. A system as in claim 14 in which said spectral power measure of each respective waveform is found only on the basis of selected coefficients of a Fourier series representation of the waveform, said selected coefficients being those which have been found most likely to differ as between the presence and absence of the stimulus for a large population of subjects believed to exhibit a significant evoked potential in response to the stimulus.

16. A system as in claim 11, 12 or 13 in which the testing means comprise means for testing relative to a rejection level and an acceptance level which are determined on the basis of: the number of averaged waveforms in the sets, a selected degree of risk that the testing will ascertain the likely presence of a significant evoked potential when in fact it is absent, and a selected degree of risk that the testing will ascertain the likely absence of a significant evoked potential when in fact it is present.

17. A system as in claim 11, 12 or 13 in which the stimulus is an auditory stimulus.

18. A system as in claim 11, 12 or 13 in which the stimulus is selected from the group consisting of auditory, visual and somatosensory stimuli.

19. A system as in claim 18 in which the evoked potential is indicative of response to the stimulus selected from the group consisting of brainstem and cortical responses.

20. A method comprising the steps of:
(a) deriving a first brainwave in the absence of a stimulus;
(b) sampling the brainwave to produce digital samples $DP(i)$ of the brainwave to form an epoch $n=1$, repeating to form an epoch $n=2$, and repeating to form a total of N epochs, where $n=1, 2, \ldots, N$, and forming the N epochs into a group K;
(c) finding for the group K produced in the immediately preceding step an averaged waveform K;
(d) deriving a second brainwave for the same subject in the presence of the stimulus;
(e) repeating steps (b) and (c) for the second brainwave;
(f) repeating the sequence of steps (a) through (e) for successive first and second brainwaves to produce for each a respective sequence of groups $K=2$, $K=3, \ldots, K=K(min)$, and producing for each repetition a respective pair of averaged waveforms K, a respective spectral measure $P(K)$ for the absence of the stimulus and a respective spectral measure $P'(K)$ for the presence of the stimulus;
(g) finding a test measure $V(K)$ as a function of the difference between said spectral measure $P(K)$ and $P'(K)$ derived from said waveforms and of the variance thereof;
(h) finding an acceptance level $Va(K)$ and a rejection level $Vr(K)$ as respective functions of at least the number of groups K for which said spectral measures have been found;
(i) evaluating the test measure relative to said acceptance and rejection levels to determine if the difference between the first and second averaged waveforms, as reflected in said test measure V(K), is likely to correspond to the presence of a significant evoked potential in response to said stimulus, or to the absence of said potential, or to an uncertainty as to the presence or absence of said potential;

(j) in case the determination results in a finding of uncertainty, repeating the sequence of steps (a) through (i) using successively incremented values of K(min) in step (f) until step (i) yields a determination of either the likely presence of said potential or steps (a) through (i) have been repeated a selected maximum number of times such that K=K(max); and (k) producing a tangible representation of said determination.

* * * * *